(12) United States Patent
Kassab

(10) Patent No.: US 8,897,869 B2
(45) Date of Patent: *Nov. 25, 2014

(54) PLAQUE TYPE DETERMINATION DEVICES, SYSTEMS, AND METHODS

(75) Inventor: Ghassan S. Kassab, Newport Coast, CA (US)

(73) Assignee: 3DT Holdings, LLC, San Diego, CA (US)

( * ) Notice: Subject to any disclaimer, the term of this patent is extended or adjusted under 35 U.S.C. 154(b) by 778 days.

This patent is subject to a terminal disclaimer.

(21) Appl. No.: 12/906,412

(22) Filed: Oct. 18, 2010

(65) Prior Publication Data

US 2011/0034824 A1 Feb. 10, 2011

Related U.S. Application Data

(63) Continuation of application No. 11/063,836, filed on Feb. 23, 2005, now Pat. No. 7,818,053, which is a continuation-in-part of application No. 10/782,149, filed on Feb. 19, 2004, now Pat. No. 7,454,244.

(60) Provisional application No. 60/449,266, filed on Feb. 21, 2003, provisional application No. 60/493,145, filed on Aug. 7, 2003, provisional application No. 60/502,139, filed on Sep. 11, 2003.

(51) Int. Cl.
| A61B 5/05 | (2006.01) |
| A61B 5/053 | (2006.01) |
| A61B 5/02 | (2006.01) |
| A61B 17/00 | (2006.01) |
| A61B 5/107 | (2006.01) |

(52) U.S. Cl.
CPC ....... *A61B 5/053* (2013.01); *A61B 2017/00026* (2013.01); *A61B 5/0538* (2013.01); *A61B 5/02007* (2013.01); *A61B 5/1076* (2013.01)
USPC ........................................................ 600/547

(58) Field of Classification Search
USPC ......... 600/547, 486, 585, 481, 454, 505, 526, 600/587, 561, 483; 606/41, 192, 194, 198; 128/898; 424/439; 623/1.11
See application file for complete search history.

(56) References Cited

U.S. PATENT DOCUMENTS

| 3,896,373 A | 7/1975 | Zelby |
| 4,380,237 A | 4/1983 | Newbower |

(Continued)

FOREIGN PATENT DOCUMENTS

| EP | 1 025 805 | 8/2000 |
| WO | WO 98/35611 | 8/1998 |

(Continued)

OTHER PUBLICATIONS

International Searching Authority, International Search Report, mailed Aug. 16, 2012 (PCT/US2011/023911).

(Continued)

*Primary Examiner* — Brian Szmal
(74) *Attorney, Agent, or Firm* — Reichel IP LLP; Mark C. Reichel; Natalie J. Dean

(57) ABSTRACT

Plaque type determination devices, systems, and methods. In at least one exemplary embodiment of a device for assessing composition of a plaque of the present disclosure, the device comprises an elongate body having a longitudinal axis and a distal end, a first excitation electrode and a second excitation electrode located along the longitudinal axis of the body near the distal end of the elongate body, and a first detection electrode and a second detection electrode along the longitudinal axis of the body and in between the first and second excitation electrodes, wherein when a current source in communication with at least one of the first excitation electrode and the second excitation electrode applies current thereto to facilitate measurement of two or more conductance values within a vessel containing at least part of the elongate body at or near a plaque site, a plaque type determination can be made based upon a calculation of tissue conductance using at least one of the two or more conductance values.

22 Claims, 8 Drawing Sheets

(56) References Cited

U.S. PATENT DOCUMENTS

| | | | |
|---|---|---|---|
| 4,587,975 | A | 5/1986 | Salo |
| 4,840,182 | A | 6/1989 | Carlson |
| 4,957,110 | A | 9/1990 | Vogel et al. |
| 5,058,583 | A | 10/1991 | Geddes et al. |
| 5,125,410 | A | 6/1992 | Misono et al. |
| 5,233,994 | A | 8/1993 | Shmulewitz |
| 5,366,443 | A | 11/1994 | Eggers et al. |
| 5,453,576 | A | 9/1995 | Krivitski |
| 5,665,103 | A | 9/1997 | Lafontaine et al. |
| 5,827,192 | A | 10/1998 | Gopakumaran et al. |
| 5,842,998 | A | 12/1998 | Gopakumaran et al. |
| 5,971,933 | A | 10/1999 | Schluter et al. |
| 6,112,115 | A | 8/2000 | Feldman et al. |
| 6,165,977 | A | 12/2000 | Mochly-Rosen |
| 6,187,744 | B1 | 2/2001 | Rooney |
| 6,191,136 | B1 | 2/2001 | Marban |
| 6,270,493 | B1 | 8/2001 | Lalonde et al. |
| 6,325,762 | B1 | 12/2001 | Tjin |
| 6,354,999 | B1 | 3/2002 | Dgany et al. |
| 6,360,123 | B1 | 3/2002 | Kimchi et al. |
| 6,398,738 | B1 | 6/2002 | Millar |
| 6,406,422 | B1 | 6/2002 | Landesberg |
| 6,471,656 | B1 | 10/2002 | Shalman et al. |
| 6,494,832 | B1 | 12/2002 | Feldman et al. |
| 6,511,413 | B2 | 1/2003 | Landesberg |
| 6,545,678 | B1 | 4/2003 | Ohazama |
| 6,569,862 | B1 | 5/2003 | Marban |
| 6,663,661 | B2 | 12/2003 | Boneau |
| 6,666,828 | B2 | 12/2003 | Greco et al. |
| 6,926,674 | B2 | 8/2005 | Tenerz et al. |
| 6,939,313 | B2 | 9/2005 | Saadat |
| 7,069,072 | B2 | 6/2006 | Jansen et al. |
| 7,141,019 | B2 | 11/2006 | Pearlman |
| 7,169,107 | B2 | 1/2007 | Jersey-Willuhn et al. |
| 7,189,208 | B1 | 3/2007 | Beatty et al. |
| 7,326,241 | B2 | 2/2008 | Jang |
| 7,818,053 | B2 * | 10/2010 | Kassab .................. 600/547 |
| 8,185,194 | B2 * | 5/2012 | Kassab .................. 600/547 |
| 2003/0149368 | A1 | 8/2003 | Hennemann et al. |
| 2003/0195504 | A1 | 10/2003 | Tallarida et al. |
| 2004/0024329 | A1 | 2/2004 | Jansen et al. |
| 2004/0116816 | A1 * | 6/2004 | Tenerz et al. .......... 600/486 |
| 2004/0254495 | A1 | 12/2004 | Mabary et al. |
| 2007/0161914 | A1 | 7/2007 | Zdeblick et al. |
| 2008/0176271 | A1 | 7/2008 | Silver et al. |
| 2008/0194996 | A1 | 8/2008 | Kassab |
| 2008/0269581 | A1 | 10/2008 | Wood et al. |
| 2009/0216133 | A1 | 8/2009 | Kassab |
| 2010/0041984 | A1 | 2/2010 | Shapeland et al. |

FOREIGN PATENT DOCUMENTS

| | | |
|---|---|---|
| WO | WO 02/19905 | 3/2002 |
| WO | WO 02/085442 | 10/2002 |
| WO | WO 03/092495 | 11/2003 |

OTHER PUBLICATIONS

International Searching Authority, Written opinion of the International Searching Authority, mailed Aug. 16, 2012 (PCT/US2011/023911).

International Searching Authority, International Search Report, mailed Aug. 30, 2012 (PCT/US2011/024961).

International Searching Authority, Written opinion of the International Searching Authority, mailed Aug. 30, 2012 (PCT/US2011/024961).

International Searching Authority, International Search Report, mailed Sep. 7, 2012 (PCT/US2011/026337).

International Searching Authority, Written opinion of the International Searching Authority, mailed Sep. 7, 2012 (PCT/US2011/026337).

Hoekstein and Inbar, "Cardiac Stroke Volume Estimation from Two Electrodes Electrical Impedance Measurements," Technion Dept. of EE Publication EE PUB No. 911, Feb. 1994.

Hettrick et al. "In Vivo Measurement of Real-Time Aortic Segmental Volume Using a Conductance Catheter." Annals of Biomedical Engineering, vol. 26, pp. 431-440,1998.

Kornet et al. "Conductance Merhod for the Measurement of the Cross-Sectional Area of the Aorta." Ann. Biom. Engr, v. 27, pp. 141-150, 1999.

Hettrick et al. "Finite Element Model Determination fo Correction Factors Used for Measurement of Aorta Diameter via Conductance." Ann. of Biom. Engr., v.27, pp. 151-159, 1999.

International Searching Authority, International Search Report and Written Opinion, PCT/US2004/004828, dated Jul. 6, 2005.

International Searching Authority, International Search Report and Written Opinion, PCT/US2006/005985, dated Aug. 8, 2007.

Supplementary European Search Report for EP Application Serial No. EP 04 71 2383 to Electro-Cat, LLC, dated Aug. 6, 2007.

PCT/US2010/031553, PCT International Preliminary Report on Patentability, dated Oct. 18, 2011.

PCT/US2010/032178, PCT International Preliminary Report on Patentability, dated Nov. 3, 2011.

* cited by examiner

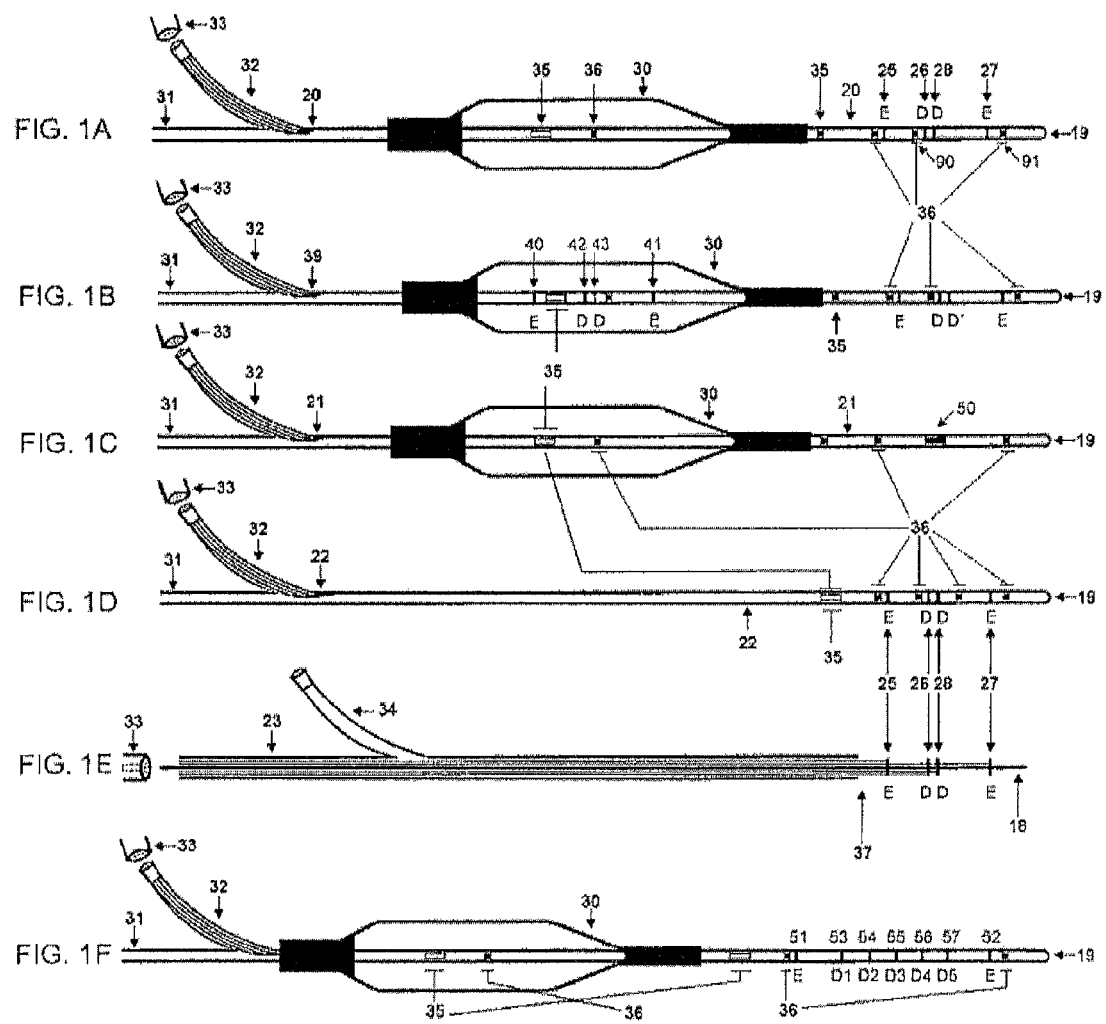

envelope data, peak-peak, of voltage at the detection electrodes

PLAQUE TYPE DETERMINATION DEVICES, SYSTEMS, AND METHODS

PRIORITY

This U.S. patent application is a continuation application of, and claims priority to, U.S. patent application Ser. No. 11/063,836, filed Feb. 23, 2005 and issued as U.S. Pat. No. 7,818,053 on Oct. 19, 2010, which is a continuation-in-part application of, and claims priority to, U.S. patent application Ser. No. 10/782,149, filed Feb. 19, 2004 and issued as U.S. Pat. No. 7,454,244 on Nov. 18, 2008, which is related to, and claims the priority benefit of, U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003. The contents of each of these applications are hereby incorporated by reference in their entirety into this disclosure.

BACKGROUND

Coronary heart disease (CHD) is commonly caused by atherosclerotic narrowing of the coronary arteries and is likely to produce angina pectoris, heart attacks or a combination. CHD caused 466,101 deaths in the USA in 1997 and is one of the leading causes of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

One common type of coronary artery disease is atherosclerosis, which is a systemic inflammatory disease of the vessel wall that affects multiple arterial beds, such as aorta, carotid and peripheral arteries, and causes multiple coronary artery lesions and plaques. Atherosclerotic plaques typically include connective tissue, extracellular matrix (including collagen, proteoglycans, and fibronectin elastic fibers), lipid (crystalline cholesterol, cholesterol esters and phospholipids), and cells such as monocyte-derived macrophages, T lymphocytes, and smooth muscles cells. A wide range of plaques occurs pathologically with varying composition of these components.

A process called "positive remodeling" occurs early on during the development of atherosclerosis in coronary artery disease (CAD) where the lumen cross-sectional area (CSA) stays relatively normal because of the expansion of external elastic membrane and the enlargement of the outer CSA. However, as CAD progresses, there is no further increase in the external diameter of the external elastic membrane. Instead, the plaque begins to impinge into the lumen and decreases the lumen CSA in a process called "negative remodeling".

Evidence shows that that a non-significant coronary atherosclerotic plaque (typically <50% stenosis) can rupture and produce myocardial infarct even before it produces significant lumen narrowing if the plaque has a particular composition. For example, a plaque with a high concentration of lipid and a thin fibrous cap may be easily sheared or ruptured and is referred to as a "vulnerable" plaque. In contrast, "white" plaques are less likely to rupture because the increased fibrous content over the lipid core provides stability ("stable" plaque). A large lipid core (typically >40%) rich in cholesterol is at a high risk for rupture and is considered a "vulnerable" plaque. In summary, plaque composition appears to determine the risk of acute coronary syndrome more so than the standard degree of stenosis because a higher lipid core is a basic characteristic of a higher risk plaque.

Conventionally, angiography has been used to visualize and characterize atherosclerotic plaque in coronary arteries. Because of the recent finding that plaque composition, rather than severity of stenosis, determines the risk for acute coronary syndromes, newer imaging modalities are required to distinguish between and determine the composition of "stable" and "vulnerable" plaques. Although a number of invasive and noninvasive imaging techniques are available to assess atherosclerotic vessels, most of the standard techniques identify luminal diameter, stenosis, wall thickness and plaque volume. To date, there is no standard method that can characterize plaque composition (e.g., lipid, fibrous, calcium, or thrombus) and therefore there is no routine and reliable method to identify the higher risk plaques.

Noninvasive techniques for evaluation of plaque composition include magnetic resonance imaging (MRI). However, MRI lacks the sufficient spatial resolution for characterization of the atherosclerotic lesion in the coronary vessel. Minimally invasive techniques for evaluation of plaque composition include intravascular ultrasound (IVUS), optical coherence tomography (OCT), raman and infrared spectroscopy. Thermography is also a catheter-based technique used to detect the vulnerable plaques on the basis of temperature difference caused by the inflammation in the plaque. Using the various catheter-based techniques requires a first step of advancement of an IVUS, OCT, or thermography catheter and then withdrawal of the catheter before coronary angioplasty thereby adding additional time and steps to the stent procedure. Furthermore, these devices require expensive machinery and parts to operate. This adds significant cost and time and more risk to the procedure.

Thus, a need exists in the art for an alternative to the conventional methods of determining plaque type. A further need exist for a reliable, accurate and minimally invasive system or technique of determining a plaque type or composition within a given blood vessel.

BRIEF SUMMARY

In at least one exemplary embodiment of a device for assessing composition of a plaque of the present disclosure, the device comprises an elongate body having a longitudinal axis and a distal end, a first excitation electrode and a second excitation electrode located along the longitudinal axis of the body near the distal end of the elongate body, and a first detection electrode and a second detection electrode along the longitudinal axis of the body and in between the first and second excitation electrodes, wherein when a current source in communication with at least one of the first excitation electrode and the second excitation electrode applies current thereto to facilitate measurement of two or more conductance values within a vessel containing at least part of the elongate body at or near a plaque site, a plaque type determination can be made based upon a calculation of tissue conductance using at least one of the two or more conductance values. In another embodiment, the elongate body comprises a wire. In yet another embodiment, the measurement of two or more conductance values is/are made using at least one of the first detection electrode and a second detection electrode.

In at least one exemplary embodiment of a device for assessing composition of a plaque of the present disclosure, a first distance between the first excitation electrode and the first detection electrode is equal to a second distance between the second excitation electrode and the second detection electrode. In an additional embodiment, the measurement of two or more conductance values is/are made upon infusion of a bolus into the vessel, wherein the bolus contacts at least one of the first detection electrode and a second detection electrode. In yet an additional embodiment, the measurement of two or more conductance values is/are made upon infusion of two boluses of differing conductive concentrations into the vessel, wherein the two boluses contact at least one of the first detection electrode and a second detection electrode. In another embodiment, the two boluses comprise a first bolus comprising a first concentration of saline and a second bolus comprising a second concentration of saline, wherein the first concentration is different from the second concentration.

In at least one exemplary embodiment of a device for assessing composition of a plaque of the present disclosure, the device further comprises a tube having a lumen, the tube surrounding at least part of the elongate body. In another embodiment, the measurement of two or more conductance values is/are made upon infusion of a bolus through the tube into the vessel, wherein the bolus contacts at least one of the first detection electrode and a second detection electrode. In various embodiments, the device further comprises a suction/infusion port located near a distal end of the tube, wherein when the suction/infusion port is in communication with the lumen of the tube, one or more solutions can be injected through the lumen, through the suction/infusion port, and into the plaque site. In an additional embodiment, the device further comprises a solution source coupled to the tube for delivering a solution through the tube lumen and into the plaque site.

In at least one exemplary embodiment of a device for assessing composition of a plaque of the present disclosure, the device further comprises a data acquisition and processing system operable to receive conductance data from at least one of the first detection electrode and the second detection electrode, the data acquisition and processing system further operable to calculate tissue conductance using at least one of the two or more conductance values. In another embodiment, the first detection electrode and the second detection electrode are spaced a first distance from one another, and wherein the first detection electrode and the first excitation electrode are spaced a second distance from one another, wherein the first distance is less than the second distance. In yet another embodiment, the first excitation electrode is spaced between about 4.0 mm and 5.0 mm from the first detection electrode, and wherein the second excitation electrode is spaced between about 4.0 mm and 5.0 mm from the second detection electrode.

In at least one exemplary embodiment of a device for assessing composition of a plaque of the present disclosure, the device comprises a wire having a pair of detection electrodes located in between a pair of excitation electrodes, said wire operable to obtain one or more conductance values at a plaque site within a vessel to determine plaque type of a plaque at the plaque site. In an additional embodiment, the one or more conductance values is/are made upon infusion of a bolus into the vessel and when a current is applied to at least one of the pair of excitation electrodes.

In at least one exemplary embodiment of a device for assessing composition of a plaque of the present disclosure, the device comprises a wire having a pair of detection electrodes located in between a pair of excitation electrodes, the pair of detection electrodes operable to obtain two or more conductance values within a vessel when a current is applied to at least one of the pair of excitation electrodes and at least part of the wire is positioned in the vessel at or near a plaque site, said two or more conductance values useful to make a plaque type determination of a plaque at the plaque site. In another embodiment, the device further comprises a current source for providing current to at least one of the pair of excitation electrodes, and a solution source for delivering a solution into the vessel at or near the plaque site.

BRIEF DESCRIPTION OF THE DRAWINGS

FIG. 1A shows a balloon catheter having impedance measuring electrodes supported in front of the stenting balloon, according to an embodiment of the present disclosure;

FIG. 1B shows a balloon catheter having impedance measuring electrodes within and in front of the balloon, according to an embodiment of the present disclosure;

FIG. 1C shows a catheter having an ultrasound transducer within and in front of balloon, according to an embodiment of the present disclosure;

FIG. 1D shows a catheter without a stenting balloon, according to an embodiment of the present disclosure;

FIG. 1E shows a guide catheter with wire and impedance electrodes, according to an embodiment of the present disclosure;

FIG. 1F shows a catheter with multiple detection electrodes, according to an embodiment of the present disclosure;

DETAILED DESCRIPTION

Figure 2A:
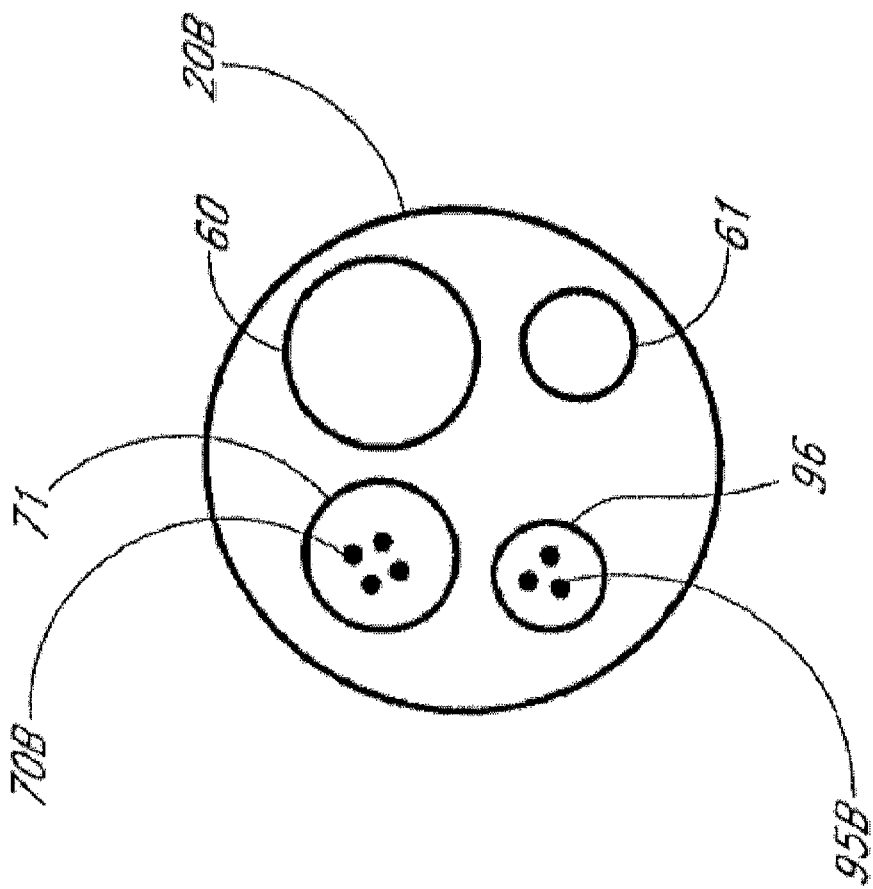
FIG. 2A shows a catheter in cross-section proximal to the location of the sensors showing the leads embedded in the material of the probe, according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure of the present application provides accurate and reproducible measurements of the type or composition of plaques in blood vessels within acceptable limits. This enables the determination of a plaque type and/or composition in order to improve patient health by allowing early treatment options for undersized (but potentially dangerous) plaques that could dislodge and cause infarcts or other health problems.

In the pending parent application, which is incorporated by reference herein in its entirety, a novel technique is introduced that allows the determination of vessel lumen CSA based on an electrical impedance principle. The technique also allows the determination of current loss through the vessel wall, for example, the parallel conductance ($G_p$). Briefly, the methodology involves a multi-injection technique including slightly hypertonic and slightly hypotonic solutions. The two injections with known conductivities allow the measurement of the total conductance for each injection (conductance in the vessel lumen and $G_p$), and hence provide two equations that couple the CSA and $G_p$. Therefore, the CSA and $G_p$ can be determined at any point along the vessel length. An objective of the present disclosure is to determine the $G_p$ value and determine the plaque type from this value.

$G_p$ is a measure of electrical conductivity through the tissue and is the inverse of electrical resistivity. Fat or lipids have a higher resistivity to electrical flow or a lower $G_p$ than compared to most other issues. For example, lipids have approximately ten times (10.times.) higher resistivity or ten times (10.times.) lower conductivity than vascular tissue. In terms of conductivities, fat has a 0.023 S/m value, blood vessel wall has 0.32 S/m, and blood has a 0.7 S/m. Because unstable plaques are characterized by a higher lipid core, a purpose of this disclosure is to use the value of $G_p$ to identify vulnerable plaque.

Studies indicate that $G_p$ is about 70-80% for a normal vessel (as determined by Equation [6]). This value is significantly reduced when lipid is present in the vessel wall. In other words, the lipid insulates the vessel and significantly reduces the current loss through the wall. The degree of reduction of $G_p$ will be dependent on the fraction of lipid in the plaque. The higher the fraction of lipid, the smaller the value of $G_p$, and consequently the greater the risk of plaque rupture which can cause acute coronary syndrome. Thus, the exemplary embodiments described below and throughout this disclosure are used to develop a measure for the conductance, $G_p$, which in turn is used as a determinant of the type and/or composition of the plaque in the region of measurement.

As described below, in one exemplary embodiment, there is provided an angioplasty catheter with impedance electrodes near the distal end 19 of the catheter (e.g., in front of the balloon) for immediate measurement of the cross-sectional area of a vessel lumen during balloon advancement. This catheter includes electrodes for accurate detection of organ luminal $G_p$ and ports for pressure gradient measurements. Hence, it is not necessary to change catheters such as with the current use of intravascular ultrasound or OCT. In one exemplary embodiment, the catheter provides direct measurement of plaque type (e.g., soft/vulnerable or hard/stable), thereby allowing the selection of an appropriate balloon material (low or high pressure). In another embodiment, additional impedance electrodes may be incorporated in the center of the balloon on the catheter in order to deploy the stent to the desired cross-sectional area. The procedures described herein substantially improve the accuracy of stenting and improve the cost and outcome as well. Furthermore, they allow for proper and accurate assessment of plaque type and/or composition.

Exemplary embodiments of impedance or conductance catheters are illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. In various embodiments, electrodes 25 and 27 are spaced 4-5 mm from either side of the inner electrodes and form the outer (excitation) electrodes. Such spacing as described herein has been discovered to enhance the excitation and detection functions of the electrodes with respect to the plaque area of interest.

In one approach, dimensions of a catheter to be used for any given application depend on the optimization of the potential field using finite element analysis described below. For small organs or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In an exemplary embodiment, the detection electrodes are spaced with 0.5-1 min between them and with a distance between 4-5 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27 and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, Catheter 20 advantageously includes pressure port 90 and pressure port 91 proximal to or at the site of the cross-sectional measurement for evaluation of pressure gradients. As described below with reference to FIGS. 2A, 2B and 3, in at least one embodiment, the pressure ports are connected by respective conduits in the catheter 20 to pressure sensors in the data acquisition system 100 or 300. Such pressure sensors are well known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration may be carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27 and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56 and 57 are used to detect the current at their respective sites.

The tip of the catheter can be straight, curved or with an angle to facilitate insertion into the coronary arteries or other lumens. The distance between the balloon and the electrodes is usually small, in the 0.5-2 cm range but can be closer or further away, depending on the particular application or treatment involved.

In another embodiment, shown in FIG. 1C the catheter 21 has one or more imaging or recording device, such as, for example, ultrasound transducers 50 for cross-sectional area and wall thickness measurements. As shown in this embodiment, the transducers 50 are located near the distal tip 19 of the catheter 21.

FIG. 1D shows an embodiment of the impedance catheter 22 without an angioplastic or stenting balloon. This catheter also possesses an infusion or injection port 35 located proximal relative to the excitation electrode 25 and pressure port 36.

With reference to the embodiment shown in FIG. 1E, the electrodes 25, 26, 27, 28 can also be built onto a wire 18, such as, for example, a pressure wire, and inserted through a guide catheter 23 where the infusion of bolus can be made through the lumen of the guide catheter 37. The wires are conductively separated from each other to allow for individual recording and relay of values back to the detection system 100 or 300.

With reference to the embodiments shown in FIGS. 1A, 1B, 1C, 1D, 1E and 1F, the impedance catheter advantageously includes optional ports 35, 36, 37 for suction of contents of the organ or infusion of fluid. The suction/infusion port 35, 36, 37 can be placed as shown with the balloon or elsewhere either proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In certain embodiments, the catheter contains an extra channel for insertion of a guide wire to stiffen the flexible catheter during the insertion or data recording. Additionally, the same channel 31 may be used to inject fluid solutions of various concentrations into the plaque area of interest. An additional channel 32 may be connected to the catheter such that the electrical wires connected to the one or more electrodes on the catheter are directed through the additional channel 32 and to an assessment system, such as 100 or 300, through an adaptor interface 33, such as an impedance module plug or the like, as described in more detail below.

Figure 8:
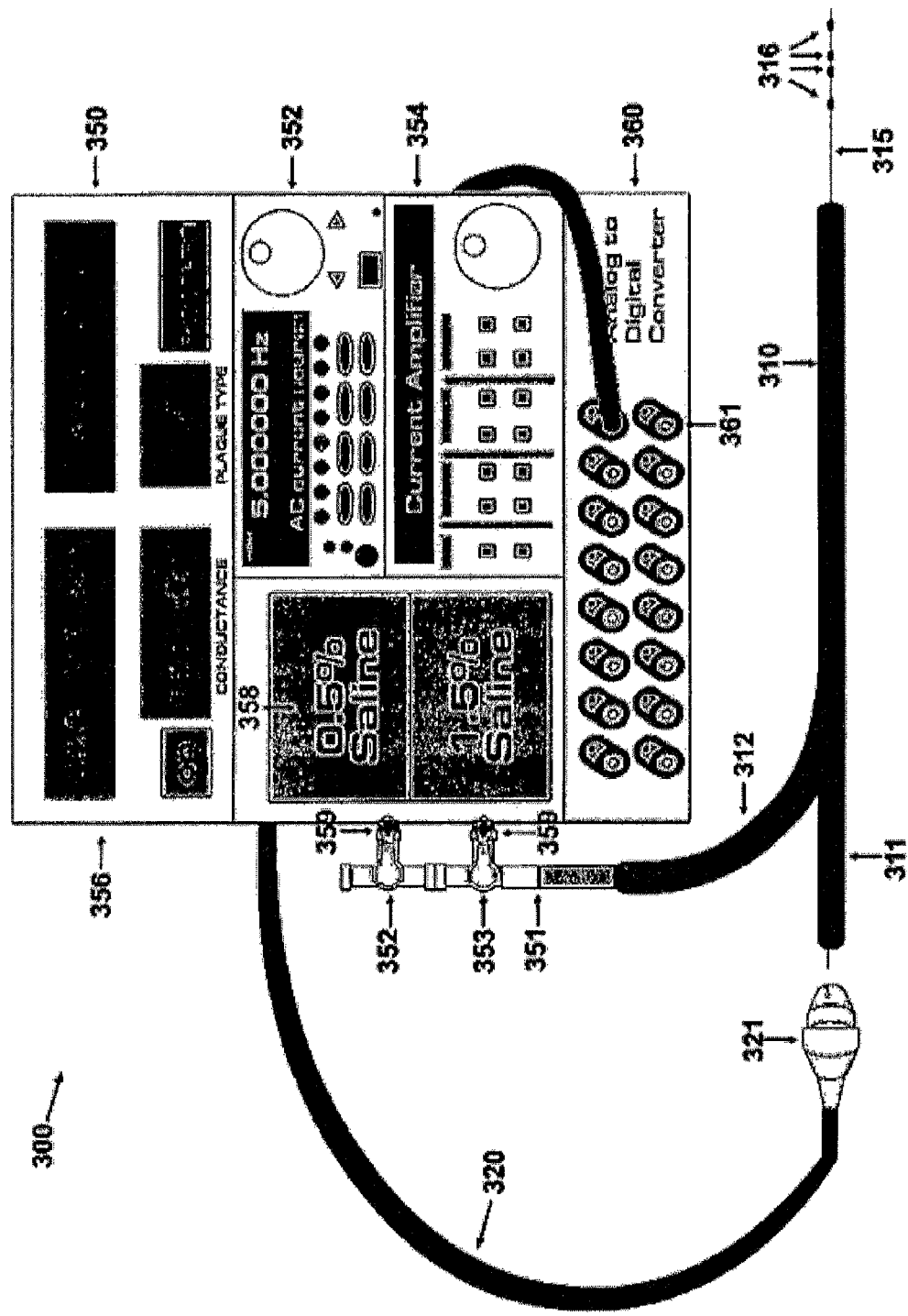
FIG. 8 shows an exemplary assessing system according to the present disclosure that measures and detects the cross sectional area and/or conductance of a plaque area.

In some embodiments, such as depicted in FIG. 1E, an adaptor interface 33 may be used to house and guide the electrical wires back to a system 100 or 300 while a side channel 34 is used to inject fluids of varying concentrations into the catheter 23. An illustration of a catheter system 300 using a catheter such as the one shown in FIG. 1E is shown in FIG. 8 and described in more detail below. Such fluid used herein may be, for example, solutions at various concentrations used to determine cross sectional area and/or conductance. In yet another embodiment (not illustrated), the catheter includes a sensor for measurement of the flow of fluid in the body organ.

Systems for Determining $G_p$ and Pressure Gradient

The Operation of the Impedance Catheter 20 is as Follows:

With reference to the embodiment shown in FIG. 1A for electrodes 25, 26, 27, 28, conductance of current flow through the vessel lumen and vessel wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue), and $C_b$ is the specific electrical conductivity of the bodily fluid which for blood generally depends on the temperature, hematocrit and orientation and deformation of blood cells and L is the distance between the detection electrodes. Equation [1] can be rearranged to solve for cross sectional area $CSA(z,t)$, with a correction factor, $\alpha$, if the electric field is non-homogeneous, as $$CSA(z, t) = \frac{L}{\alpha C_b} [G(z, t) - G_p(z, t)] \quad [1b]$$

where $\alpha$ would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that α is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z,t) = L \frac{[G_2(z,t) - G_1(z,t)]}{[C_2 - C_1]} \quad [4]$$

and $$G_p(z,t) = \frac{[C_2 \cdot G_1(z,t) - C_1 \cdot G_2(z,t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof. The value of CSA could vary through the cycle but $G_p$ does not vary significantly.

It is apparent that the total conductance is the sum of the conductance in the vessel lumen and the conductance through the vessel wall and surrounding tissue (current "leakage") as expressed by Equation [1a]. In order to assess the contribution of the current "leakage" or $G_p$, we can evaluate the contribution of $G_p$ to the total conductance as follows:

$$\% \, G_p = \frac{G_p}{\left[\frac{G_{0.5\% \, NaCl} + G_{1.5\% \, NaCl}}{2}\right]} \times 100 \quad [6]$$

where the total conductance on the denominator is taken as the average of the total conductance of the two injections.

In one approach, a pull or push through is used to reconstruct the vessel along its length. During a long injection (e.g., 10-15 s), the catheter can be pulled back or pushed forward at constant velocity U. Equation [1b] can be expressed as $$CSA(U \cdot t, t) = \frac{L}{C_b}[G(U \cdot t, t) - G_p(U \cdot (t, t))] \quad [7]$$

where the axial position, z, is the product of catheter velocity, U, and time, t; i.e., z=U·t.

For the two injections, denoted by subscript "1" and subscript "2", respectively, we can consider different time points T1, T2, etc. such that Equation [7] can be written as $$CSA_1(U \cdot T_1, t) = \frac{L}{C_1}[G_1(U \cdot T_1, t) - G_{p1}(U \cdot T_1, t)] \quad [8a]$$

$$CSA_1(U \cdot T_1, t) = \frac{L}{C_2}[G_2(U \cdot T_1, t) - G_{p1}(U \cdot T_1, t)] \quad [8b]$$

and $$CSA_2(U \cdot T_2, t) = \frac{L}{C_1}[G_1(U \cdot T_2, t) - G_{p2}(U \cdot T_2, t)] \quad [9a]$$

$$CSA_2(U \cdot T_2, t) = \frac{L}{C_2}[G_2(U \cdot T_2, t) - G_{p2}(U \cdot T_2, t)] \quad [9b]$$

and so on. Each set of Equations [8a], [8b] and [9a], [9b], etc. can be solved for $CSA_1$, $G_{p1}$ and $CSA_2$, $G_{p2}$, respectively. Hence, we can measure the CSA at various time intervals and hence of different positions along the vessel to reconstruct the length of the vessel. In an exemplary embodiment, the data on the CSA and parallel conductance as a function of longitudinal position along the vessel can be exported from an electronic spreadsheet, such as, for example, a Microsoft Excel file, to a diagramming software, such as AutoCAD, where the software uses the coordinates to render the axial variation of $G_p$ score (% $G_p$).

Furthermore, the $G_p$ score may be scaled through a scaling model index to simplify its relay of information to a user. An example of a scaling index used in the present disclosure is to designate a single digit whole number to represent the calculated conductance $G_p$ as determined by Equation [6]. In such a scaling index, "0" would designated a calculated $G_p$ of 0-9%; "1" would designate a calculated $G_p$ of 10-19%; "2" would designate a calculated $G_p$ of 20-29%; . . . ; and "9" would designate a calculated $G_p$ of 90-100%. In this scaling index example, a designation of 0, 1, 2, 3, 4, 5 or 6 would represent a risky plaque composition, with the level of risk decreasing as the scaling number increases, because the generally low level of conductance meaning generally higher fat or lipid concentrations. In contrast, a designation of 7, 8 or 9 would generally represent a non-risky plaque composition, with the level of risk decreasing as the scaling number increases, because the generally higher level of conductance meaning generally lower fat or lipid concentrations. An example of the use of this scaling index is shown in the visual display area of system 300 shown in FIG. 8.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruction the CSA and $G_p$ along the length of the 2 cm segment.

Operation of the Impedance Catheter 39:

With reference to the embodiment shown in FIG. 1B, the voltage difference between the detection electrodes 42 and 43 depends on the magnitude of the current (I) multiplied by the distance (L) between the detection electrodes and divided by the conductivity (C) of the fluid and the cross-sectional area (CSA) of the artery or other organs into which the catheter is introduced. Since the current (I), the distance (L) and the conductivity (C) normally can be regarded as calibration constants, an inverse relationship exists between the voltage difference and the CSA as shown by the following equations:

$$CSA = \frac{G \cdot L}{C} \quad [10]$$

where G is conductance expressed as the ratio of current to voltage (I/ΔV). Equation [10] is identical to Equation [1b] if we neglect the parallel conductance through the vessel wall and surrounding tissue because the balloon material acts as an insulator. This is the cylindrical model on which the conductance method is used.

As described below with reference to FIGS. 2A, 2B, 3, 4 and 5, the excitation and detection electrodes are electrically connected to electrically conductive leads in the catheter for connecting the electrodes to the data acquisition system 100 or 300.

Figure 2B:
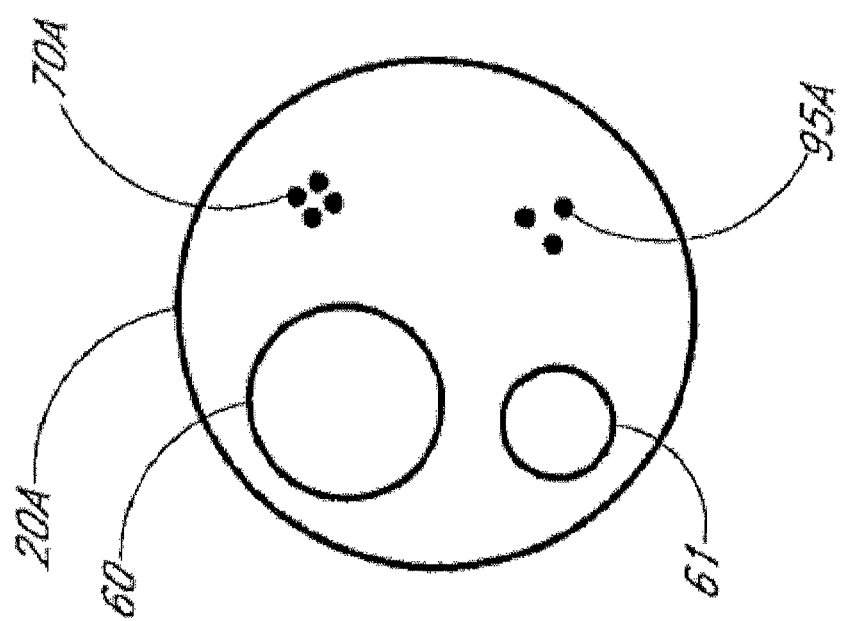
FIG. 2B shows a catheter in cross-section proximal to the location of the sensors showing the leads run in separate lumens, according to an embodiment of the present disclosure.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

Figure 3:
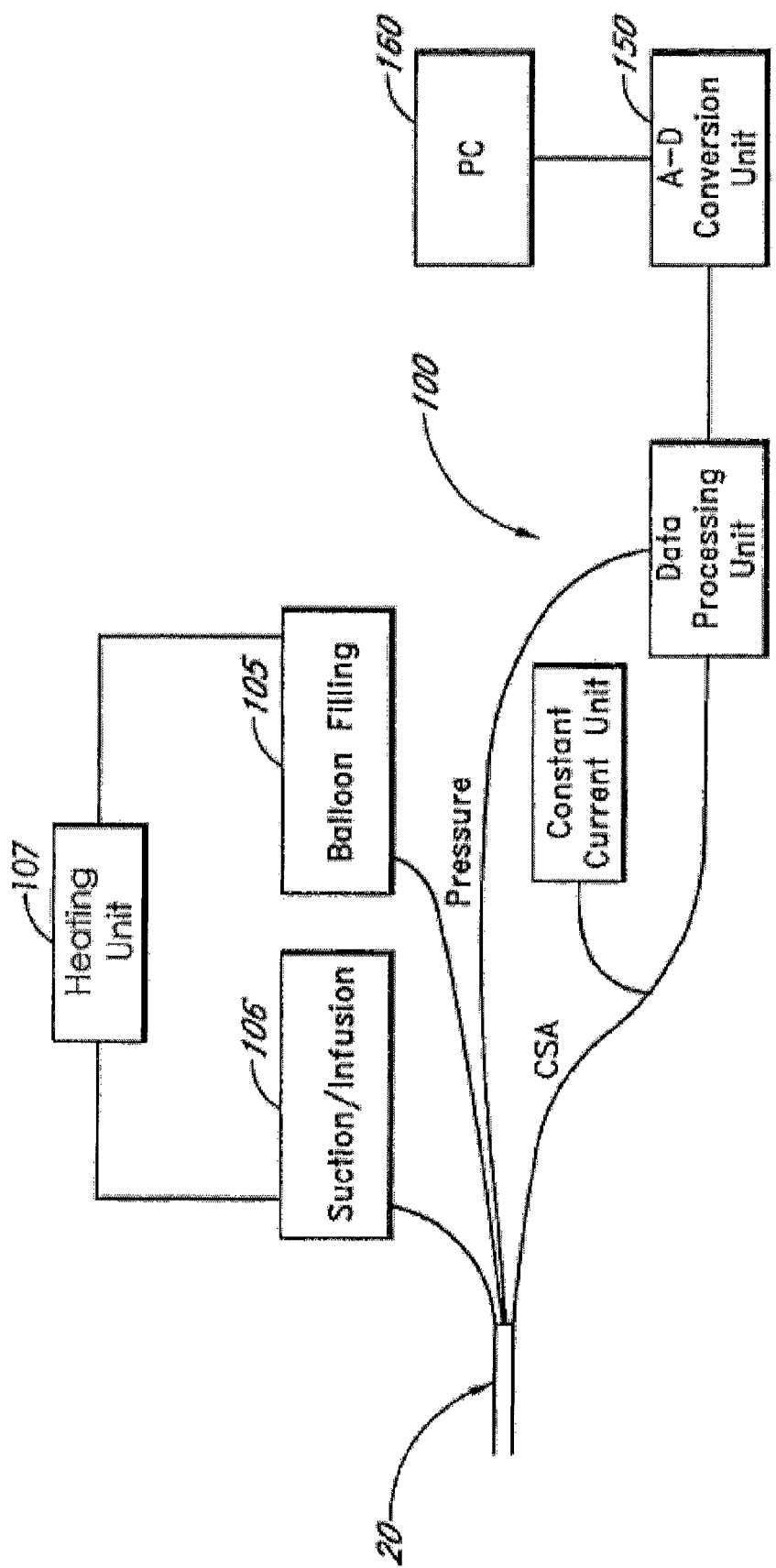
FIG. 3 is a schematic of one embodiment of the system showing a catheter carrying impedance measuring electrodes connected to the data acquisition equipment and excitation unit for the cross-sectional area measurement, according to an embodiment of the present disclosure.

With reference to FIG. 3, in one embodiment, the catheter 20 connects to a data acquisition system 100, to a manual or automatic system 105 for distension of the balloon and to a system 106 for infusion of fluid or suction of blood. The fluid can be heated to 37-39° or equivalent to body temperature with heating unit 107. The impedance planimetry system typically includes a constant current unit, amplifiers and signal conditioners. The pressure system typically includes amplifiers and signal conditioners. The system can optionally contain signal conditioning equipment for recording of fluid flow in the organ.

In one exemplary embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The CSA and parallel conductance and other relevant measures such as distensibility, tension, etc. will typically appear on the display panel in the PC module 160. Here, the user can then remove the stenosis by distension or by placement of a stent. The value of $G_p$, which reflects the "hardness" (high $G_p$) or "softness" (low $G_p$), can be used in selection of high or low pressure balloons as known in the arts.

The embodiment shown in FIG. 8 presents an example of what an overall system 300 may look like in terms of various components and optional elements. As shown in the figure, system 300 includes a control device 350, a catheter 310 and an electrical connecting tube 320. Control device 350 allows control of numerous variables through control gauges for current 352, current amplification 354, analog to digital (A/D) conversion 360 and various solution concentrations 358. Solutions at varying concentrations may be held in one or more containers attached or controlled by the solution-controlling segment 358 of control device 350. For example, such solutions may be pre-made and pre-deposited into control device 350 before the start of plaque determination analysis.

Each solution at a different concentration may be individually connected to a solution-receiving channel 312 of a catheter 310 through a solution port 351. For example, a 0.5% saline solution is connected to solution port 351 through container port 359 connected to spigot 352. A similar set up connects a 1.5% saline solution to the solution-receiving channel 312 of catheter 310 through container port 359 connected to spigot 353 flowing to solution port 351. Spigot 352 may be opened to allow the 0.5% solution flow through to the catheter while spigot 353 is closed to the flow of the 1.5% solution, and vice versa. This allows for easy and sequential control of fluid injection of various concentrations into catheter 310 without mixing, which then directs such specific concentration fluid to a plaque site as described elsewhere in this disclosure.

Furthermore, a wire 315 having one or more electrodes 316 thereon and made available to a plaque site, as described elsewhere in this disclosure, is connected to an electrical adaptor 321 that links the wire 315 to an electrical connecting tube 320 back to the control device 350 through the A/D converter area 360. One or more A/D converter connections 361 may be made available on the control device 350 to measure one or more electrical activity for one or more catheters. Thus, a multi-catheter study of multiple plaque sites may be made using a single control device 350.

All measurement and analysis results may be shown on a single display panel 356. Variables that are calculated by the internal computer using the formulas and finite element analysis described in this disclosure are displayed in real time in the display panel area 356. Exemplary display results include, but are not limited to, the cross-sectional area of the measurement sight, the temperature, the conductance value (total and/or parallel) and even a resultant determination of the plaque type by a pre-set range of conductance values that pre-classify certain plaque types, as set forth by the exemplary scaling model described above.

For example, for a given determination of a conductance value of 68% (as determined by the internal computer using Equation [6]), the resultant plaque type would be deemed as "6" or somewhat fatty. This would be a simple automated analysis of the plaque site under consideration based on the teachings and discoveries of the present disclosure as described throughout this disclosure. Of course, the range for the scaling model described above could be pre-set by the manufacturer according to established studies, but may be later changed by the individual clinic or user based on further or subsequent studies.

In use, system 300 gives the user a simple, effective and powerful tool to relay information about a vessel site and any plaque housed therein. A user would first consider the CSA level as the catheter is pulled through the site or as numerous electrodes calculate the CSA as their designated cross-sectional place, as described elsewhere in this disclosure. If there is little to no changes in the CSA value, then the user would acknowledge that there is little to no obstructions or plaques within the lumen of the blood vessel. However, if there is some change in the value of the CSA, then the conductance measurement and plaque type information is monitored to determine the extent to which plaque formation is present as well as the type of plaque, as determined by the scaling model whole number displayed, as described above.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying the 2D or 3D-geometry of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_w$ is the wall area of the organ and $C_w$ is the electrical conductivity through the wall. This equation can be solved for the wall $CSA_w$ as $$CSA_w = \frac{G_p \cdot L}{C_w} \quad [11b]$$

For a cylindrical organ, the wall thickness, h, can be expressed as $$h = \frac{CSA_w}{\pi D} \quad [12]$$

where D is the diameter of the vessel which can be determined from the circular CSA ($D=[4CSA/\pi]^{1/2}$).

When the CSA, pressure, wall thickness, and flow data are determined according to the embodiments outlined above, it is possible to compute the compliance (e.g., $\Delta CSA/\Delta P$), tension (e.g., $P \cdot r$, where P and r are the intraluminal pressure and radius of a cylindrical organ), stress (e.g., $P \cdot r/h$ where h is the wall thickness of the cylindrical organ), strain (e.g., $(C-C_d)/C_d$ where C is the inner circumference and $C_d$ is the circumference in diastole) and wall shear stress (e.g., $4 \mu Q/r^3$ where $\mu$, Q and r are the fluid viscosity, flow rate and radius of the cylindrical organ for a fully developed flow). These quantities can be used in assessing the mechanical characteristics of the system in health and disease.

To consider a method of measuring $G_p$ and related impedance, which are used to evaluate the type and/or composition of a plaque, a number of approaches may be used. In one approach, $G_p$ is measured by introducing a catheter from an exteriorly accessible opening into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In another approach, a minimum of two injections (with different concentrations and/or conductivities of NaCl) is required to solve for the two unknowns, CSA and $G_p$. In another approach, three injections will yield three sets of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one exemplary approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

To validate the measurement of $G_p$ with the measurement of CSA, the protocol and results are described here for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance (G=I/V). The conductivity of each solution was calibrated with six different tubes of known CSA at body temperature. A model using Equation [10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a sampling frequency of 75 KHz, with two channels—the current injected and the detected voltage, respectively. The current injected has a frequency of 5 KHz, so the voltage detected, modulated in amplitude by the impedance changing through the bolus injection will have a spectrum in the vicinity of 5 KHz.

Figure 4A:
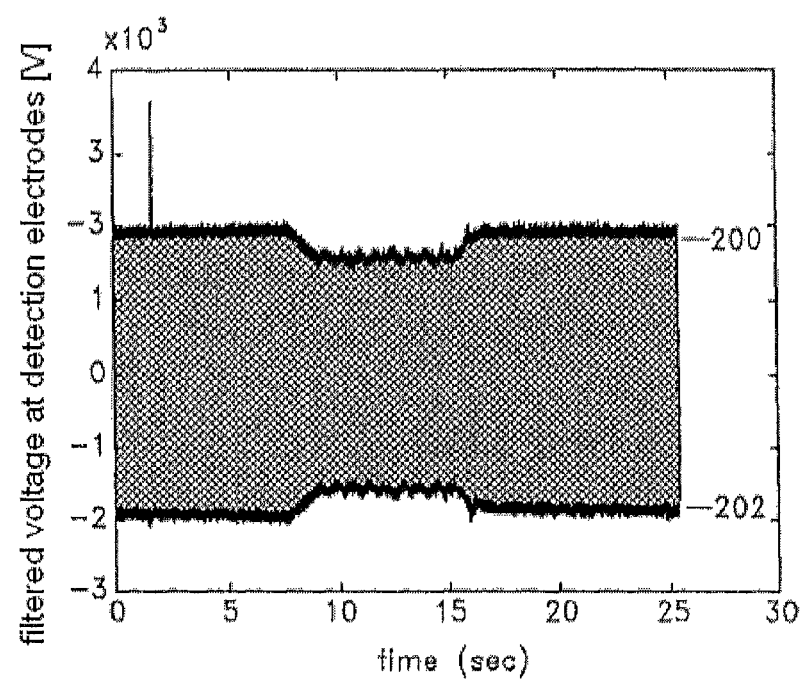
FIG. 4A shows the detected filtered voltage drop as measured in the blood stream before and after injection of 1.5% NaCl solution, according to an embodiment of the present disclosure.
Figure 4B:
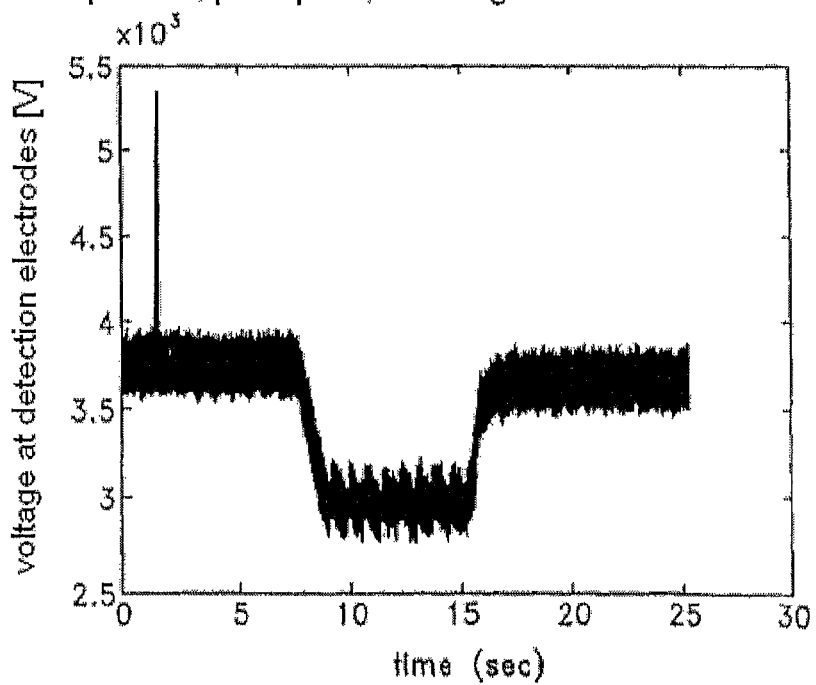
FIG. 4B shows the peak-to-peak envelope of the detected voltage shown in FIG. 4A, according to an embodiment of the present disclosure.
Figure 5A:
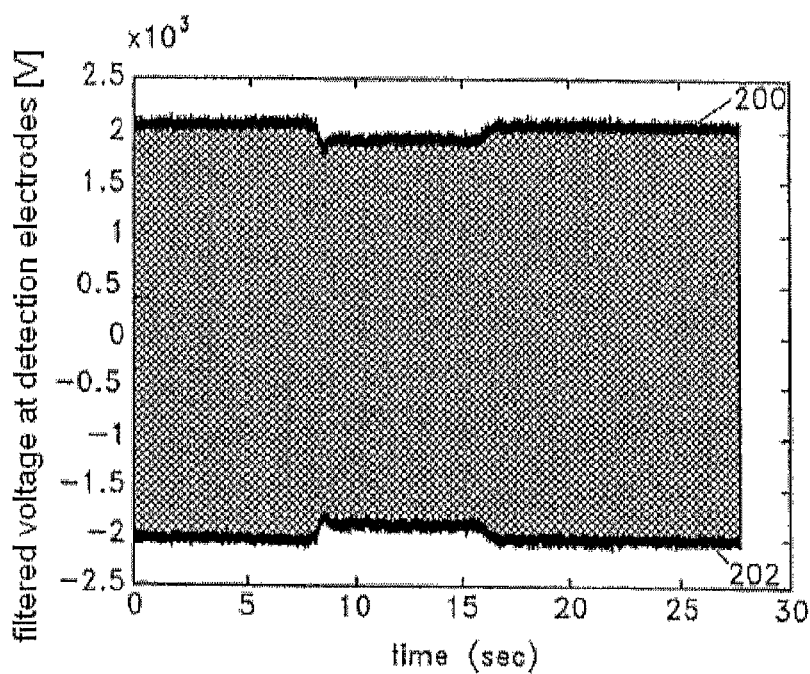
FIG. 5A shows the detected filtered voltage drop as measured in the blood stream before and after injection of 0.5% NaCl solution, according to an embodiment of the present disclosure.
Figure 5B:
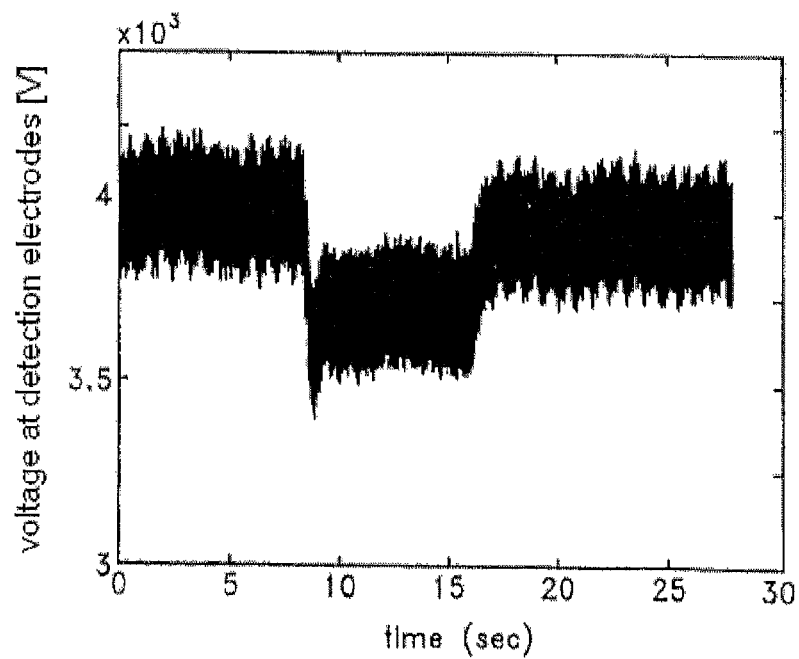
FIG. 5B shows the peak-to-peak envelope of the detected voltage shown in FIG. 5A, according to an embodiment of the present disclosure.

With reference to FIG. 4A there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B shows similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively).

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs that may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an error in the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the CSA.

Figure 6:
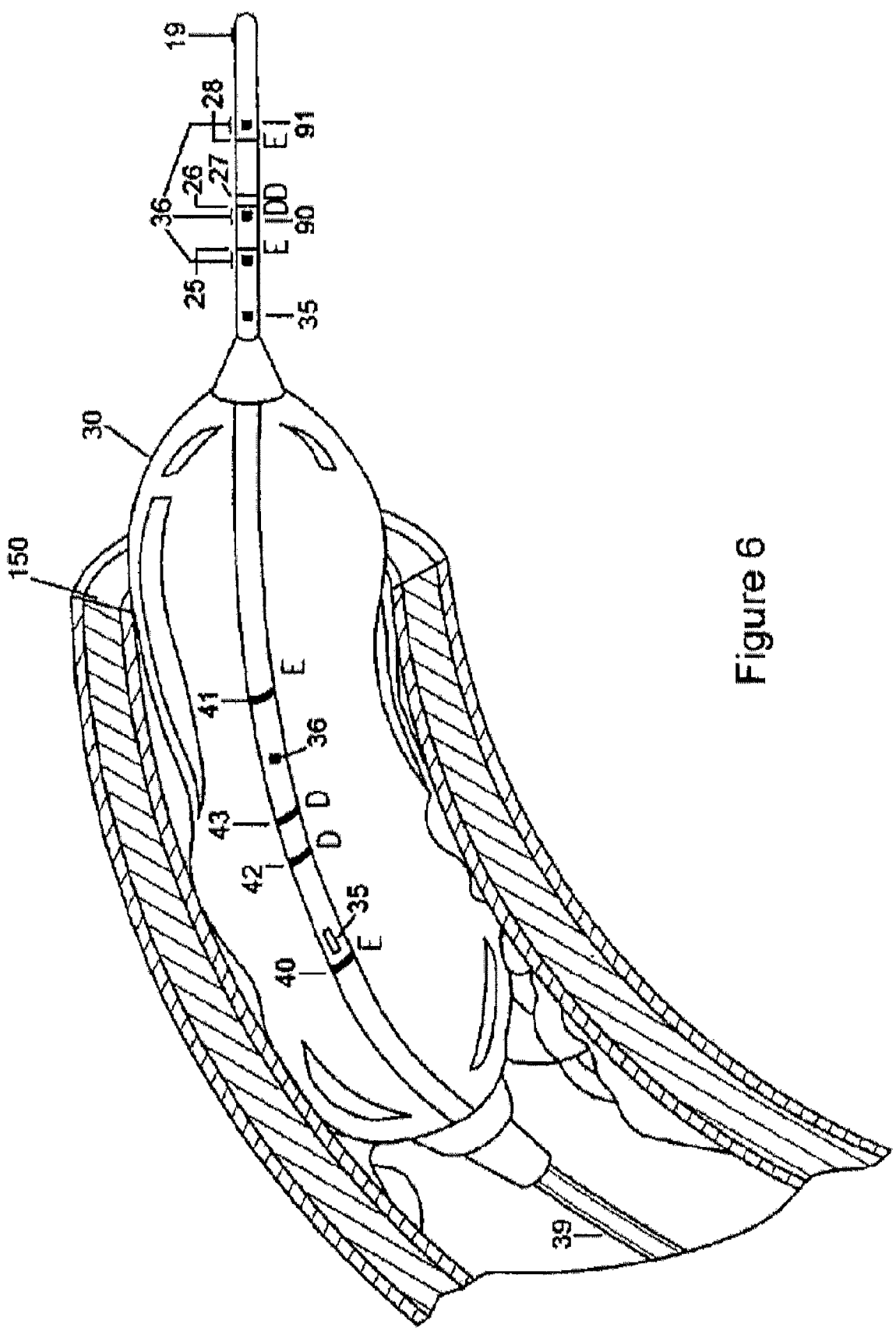
FIG. 6 shows balloon distension of the lumen of the coronary artery, according to an embodiment of the present disclosure.
Figure 7:
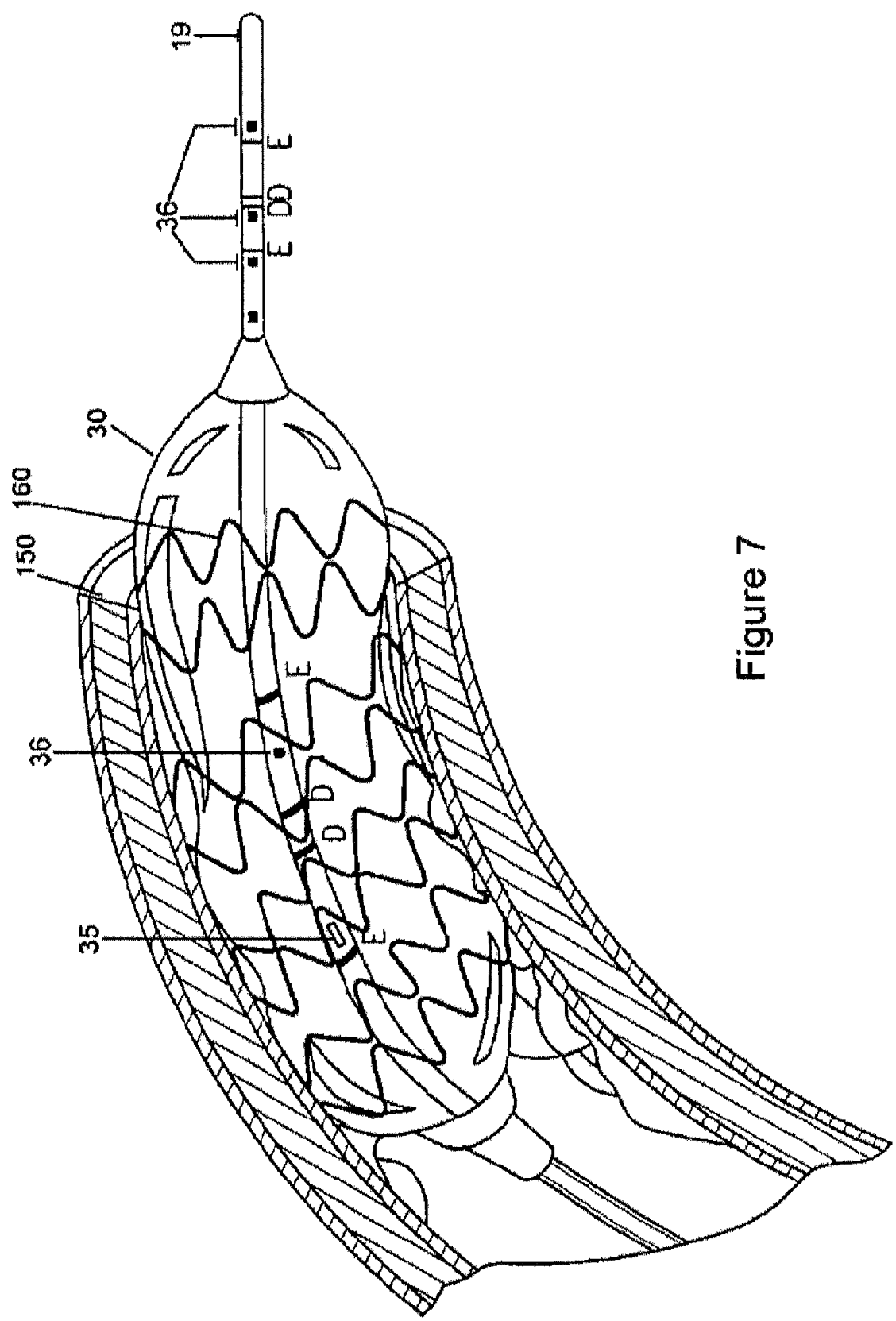
FIG. 7 shows balloon distension of a stent into the lumen of the coronary artery, according to an embodiment of the present disclosure.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7, the angioplasty balloon 30 is used to distend the stent 160 within blood vessel 150.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and catheters described herein can be applied to any body lumen or treatment site. For example, the methods, systems, and catheters described herein can be applied to any one of the following exemplary bodily hollow systems: the cardiovascular system including the heart; the digestive system; the respiratory system; the reproductive system; and the urogenital tract.

Finite Element Analysis:

In one exemplary approach, finite element analysis (FEA) is used to verify the validity of Equations [4] and [5]. There are two major considerations for the model definition: geometry and electrical properties. The general equation governing the electric scalar potential distribution, V, is given by Poisson's equation as:

$$\nabla \cdot (C \nabla V) = -I \quad [13]$$

where C, I and $\nabla$ are the conductivity, the driving current density and the del operator, respectively. Femlab or any standard finite element packages can be used to compute the nodal voltages using Equation [13]. Once V has been determined, the electric field can be obtained from as $E = \times \nabla V$.

The FEA allows the determination of the nature of the field and its alteration in response to different electrode distances, distances between driving electrodes, wall thicknesses and wall conductivities. The percentage of total current in the lumen of the vessel (% I) can be used as an index of both leakage and field homogeneity. Hence, the various geometric and electrical material properties can be varied to obtain the optimum design; i.e., minimize the non-homogeneity of the field. Furthermore, we simulated the experimental procedure by injection of the two solutions of NaCl to verify the accuracy of Equation [4]. Finally, we assessed the effect of presence of electrodes and catheter in the lumen of vessel. The error terms representing the changes in measured conductance due to the attraction of the field to the electrodes and the repulsion of the field from the resistive catheter body were quantified.

The Poisson's equation was solved for the potential field, which takes into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one exemplary approach, one or more of conditions (1)-(3) described above are met to increase the accuracy of the cylindrical model.

While various embodiments of plaque type determination devices, systems, and methods have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

I claim:

1. A device for assessing composition of a plaque, the device comprising:
   an elongate body having a longitudinal axis and a distal end;
   a first excitation electrode and a second excitation electrode located along the longitudinal axis of the body; and
   a first detection electrode and a second detection electrode along the longitudinal axis of the body and in between the first and second excitation electrodes;
   wherein when a current source in communication with at least one of the first excitation electrode and the second excitation electrode applies current thereto to facilitate measurement of two or more conductance values within a vessel containing at least part of the elongate body at a plaque site, a plaque type determination from at least two types of plaques to distinguish one plaque type from another can be made based upon a calculation of tissue conductance using at least one of the two or more conductance values obtained by the device configured to obtain said values.

2. The device of claim 1, wherein the elongate body comprises a wire.

3. The device of claim 1, wherein the measurement of two or more conductance values is/are made using at least one of the first detection electrode and a second detection electrode.

4. The device of claim 1, wherein the plaque type determination identifies a plaque at the plaque site as being at least partially fatty if the value of % $G_p$ as determined by $$\% \, G_p = \frac{G_p}{\left[\frac{G_A + G_B}{2}\right]} \times 100$$

is less than a threshold percentage, wherein A is a first concentration of saline and B is a second concentration of saline different from the first concentration of saline.

5. The device of claim 4, wherein A equals 0.5% saline, and wherein B equals 1.5% saline.

6. The device of claim 1, wherein a first distance between the first excitation electrode and the first detection electrode is equal to a second distance between the second excitation electrode and the second detection electrode.

7. The device of claim 1, wherein the measurement of two or more conductance values is/are made upon infusion of a first bolus into the vessel, wherein the first bolus contacts at least one of the first detection electrode and a second detection electrode.

8. The device of claim 1, wherein the measurement of two or more conductance values is/are made upon infusion of two boluses of differing conductive concentrations into the vessel, wherein the two boluses contact at least one of the first detection electrode and a second detection electrode.

9. The device of claim 7, wherein the first bolus comprises a first concentration of saline.

10. The device of claim 1, further comprising:
a tube having a lumen, the tube surrounding at least part of the elongate body.

11. The device of claim 10, wherein the measurement of two or more conductance values is/are made upon infusion of a bolus through the tube into the vessel, wherein the bolus contacts at least one of the first detection electrode and a second detection electrode.

12. The device of claim 10, further comprising:
a suction/infusion port located at a distal end of the tube, wherein when the suction/infusion port is in communication with the lumen of the tube, one or more solutions can be injected through the lumen, through the suction/infusion port, and into the plaque site.

13. The device of claim 10, further comprising:
a solution source coupled to the tube for delivering a solution through the tube lumen and into the plaque site.

14. The device of claim 1, further comprising:
a data acquisition and processing system operable to receive conductance data from at least one of the first detection electrode and the second detection electrode, the data acquisition and processing system further operable to calculate tissue conductance using at least one of the two or more conductance values.

15. The device of claim 1, wherein the first detection electrode and the second detection electrode are spaced at or between 0.5 mm and 1.0 mm from each other.

16. The device of claim 1, wherein the first detection electrode and the second detection electrode are spaced a first distance from one another, and wherein the first detection electrode and the first excitation electrode are spaced a second distance from one another, wherein the first distance is less than the second distance.

17. The device of claim 1, wherein the first excitation electrode is spaced at or between 4.0 mm and 5.0 mm from the first detection electrode, and wherein the second excitation electrode is spaced at or between 4.0 mm and 5.0 mm from the second detection electrode.

18. A device for assessing composition of a plaque, the device comprising:
a wire having a pair of detection electrodes located in between a pair of excitation electrodes, the pair of detection electrodes spaced at or between 0.5 mm and 1.0 mm from each other, said wire operable and configured to obtain one or more conductance values at a plaque site within a vessel to distinguish one type of a plaque from another at the plaque site.

19. The device of claim 18, wherein the one or more conductance values is/are made upon infusion of a bolus into the vessel and when a current is applied to at least one of the pair of excitation electrodes.

20. The device of claim 18, further comprising:
a data acquisition and processing system operable to receive conductance data from at least one of the first detection electrode and the second detection electrode, the data acquisition and processing system further operable to calculate tissue conductance using the one or more conductance values.

21. A device for assessing composition of a plaque, the device comprising:
a wire having a pair of detection electrodes located in between a pair of excitation electrodes, the pair of detection electrodes operable and configured to obtain two or more conductance values within a vessel when a current is applied to at least one of the pair of excitation electrodes and at least part of the wire is positioned in the vessel at a plaque site, said two or more conductance values useful to make a plaque type determination from at least two types of plaques of a plaque at the plaque site to distinguish one plaque type from another.

22. The device of claim 21, further comprising:
a current source for providing current to at least one of the pair of excitation electrodes; and
a solution source for delivering a solution into the vessel at the plaque site.

* * * * *